United States Patent
Steynberg et al.

(10) Patent No.: US 6,265,452 B1
(45) Date of Patent: Jul. 24, 2001

(54) PROCESS FOR PRODUCING LIQUID AND, OPTIONALLY, GASEOUS PRODUCTS FROM GASEOUS REACTANTS

(75) Inventors: André Peter Steynberg, Vanderbijlpark (ZA); David H. Jones, Newton; Roy W. Silverman, Winchester, both of MA (US)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 0 days.

(21) Appl. No.: 09/537,442

(22) Filed: Mar. 27, 2000

Related U.S. Application Data

(63) Continuation of application No. PCT/GB98/02946, filed on Oct. 1, 1998.

(30) Foreign Application Priority Data

Oct. 7, 1997 (ZA) .................................................. 97/8966

(51) Int. Cl.[7] .................................................. C07C 27/00
(52) U.S. Cl. ........................ 518/700; 518/706; 518/728
(58) Field of Search .................................. 518/700, 706, 518/728

(56) References Cited

U.S. PATENT DOCUMENTS

| | | | |
|---|---|---|---|
| 3,310,367 | 3/1967 | Mavrovic | 23/61 |
| 3,890,399 | 6/1975 | Gehrmann et al. | 260/654 R |
| 5,080,871 | 1/1992 | Adams et al. | 422/187 |
| 5,449,501 | 9/1995 | Luebke et al. | 422/193 |

FOREIGN PATENT DOCUMENTS

| 9414735 | 2/1994 | (WO) . |
|---|---|---|
| 976993 | 2/1998 | (ZA) . |

Primary Examiner—Johann Richter
Assistant Examiner—J. Parsa
(74) Attorney, Agent, or Firm—Ladas & Parry

(57) ABSTRACT

A process for producing liquid and gaseous products from gaseous reactants. The process includes a) feeding a synthesis gas stream of mainly carbon monoxide and hydrogen, as gaseous reactants, into a slurry bed of solid Fischer-Tropsch catalyst particles suspended in a suspension liquid, with the slurry bed being provided in a reaction zone, b) allowing the gaseous reactants to react, by means of Fischer-Tropsch synthesis, as they pass upwardly through the slurry bed; c) withdrawing liquid phase from the slurry bed, to maintain the slurry bed at a desired level; d) allowing gaseous products and unreacted gaseous reactants to disengage from the slurry bed and to pass upwardly as a gas phase into a freeboard zone of a head space above the reaction zone; e) subjecting the gas phase to distillation; f) returning separated catalyst particles and liquid phase from the distillation zone and g) withdrawing treated gas phase from the head space.

16 Claims, 3 Drawing Sheets

PROCESS FOR PRODUCING LIQUID AND, OPTIONALLY, GASEOUS PRODUCTS FROM GASEOUS REACTANTS

This application is a continuation of International Application PCT/GB98/02946 filed on Oct. 1, 1998 and which claims the benefit thereof.

THIS INVENTION relates to a process for producing liquid and, optionally, gaseous products from gaseous reactants. It relates also to an installation for producing liquid and, optionally, gaseous products from gaseous reactants.

According to a first aspect of the invention, there is provided a process for producing liquid and, optionally, gaseous products from gaseous reactants, which process comprises feeding, at a low level, gaseous reactants into a slurry bed of solid particles suspended in a suspension liquid;

allowing the gaseous reactants to react as they pass upwardly through the slurry bed, thereby to form liquid and, optionally, gaseous products, with the gaseous reactants and any gaseous product assisting in maintaining the solid particles in suspension in the suspension liquid, and with the liquid product forming, together with the suspension liquid, a liquid phase of the slurry bed;

withdrawing liquid phase from the slurry bed, to maintain the slurry bed at a desired level;

allowing any gaseous product and unreacted gaseous reactants to disengage from the slurry bed and to pass upwardly, together with any entrained solid particles and liquid phase, as a gas phase into a head space above the slurry bed;

treating the gas phase by subjecting it to distillation and, optionally, washing in the head space, thereby to separate any entrained solid particles and liquid phase from the gas phase;

returning any separated entrained solid particles and, optionally, liquid phase to the slurry bed; and withdrawing the treated gas phase from the head space.

While it is believed that the process can, at least in principle, have broader application, it is envisaged that the solid particles will normally be catalyst particles for catalyzing the reaction of the gaseous reactants into the liquid product, and, when applicable, the gaseous product; the suspension liquid will normally, but not necessarily always, be the liquid product; and that the slurry bed and the head space will normally be provided in a slurry reactor or bubble column.

The slurry bed is thus contained or provided in a reaction zone of the slurry reactor or bubble column, with the distillation being effected in a distillation zone thereof spaced from the slurry bed by a freeboard zone. In other words, the headspace comprises the freeboard zone immediately above the reaction zone, and the distillation zone above the freeboard zone.

The slurry reactor or bubble column thus uses a three phase system, ie solid catalyst particles; liquid product; and gaseous reactants and, optionally, gaseous product.

Furthermore, while it is also believed that, in principle, the process can have broader application, it is envisaged that it will have particular application in hydrocarbon synthesis where the gaseous reactants are capable of reacting catalytically in the slurry bed to form liquid hydrocarbon product(s) and, optionally, gaseous hydrocarbon product(s). In particular, the hydrocarbon synthesis may be Fischer-Tropsch synthesis, with the gaseous reactants being in the form of a synthesis gas stream comprising mainly carbon monoxide and hydrogen, and with both liquid and gaseous hydrocarbon products being produced.

The catalyst of the catalyst particles can be any desired Fischer-Tropsch catalyst, such as an iron-based catalyst, a cobalt-based catalyst, or any other Fischer-Tropsch catalyst. The catalyst particles may have a desired particle size range, eg no particles greater than 300 microns and less than 5% by mass of the particles being smaller than 22 microns.

The slurry reactor or bubble column will thus be maintained at normal elevated pressure and temperature conditions associated with Fischer-Tropsch synthesis reactions, eg a predetermined operating pressure in the range 10 to 50 bar, and a predetermined temperature in the range 160° C. and 280° C., or even higher for the production of lower boiling point product.

The catalyst particles in the slurry bed are thus maintained in suspension by the turbulence created by the synthesis gas stream and any gaseous hydrocarbon products that are formed, passing through the slurry bed, ie bubbling through the slurry bed. optionally, the slurry bed may also be mixed, eg by using mixing devices such as draft tubes or downcomers, to assist in maintaining the catalyst particles in suspension. The gas velocity through the slurry bed is thus sufficiently high to maintain the slurry bedin a state of turbulence or suspension. Draft tubes or downcomers can be used to ensure a more uniform suspension of solids throughout the slurry bed.

The gas phase entering the head space will normally comprise or consist of non-condensible unreacted gaseous reactants, a non-condensible gaseous hydrocarbon fraction, entrained solid catalyst particles, entrained liquid hydrocarbon product, a vapourized liquid hydrocarbon fraction, a condensible gaseous hydrocarbon fraction, and water vapour. The entrained solid catalyst particles will normally be associated with the entrained liquid product in the form of slurry droplets. The treated gas phase which is withdrawn from the distillation zone will normally comprise or consist of the non-condensible unreacted gaseous reactants, the non-condensible gaseous hydrocarbon fraction, the condensible gaseous hydrocarbon fraction, and the water vapour.

The gaseous hydrocarbon products thus comprise the non-condensible gaseous hydrocarbon fraction, the vapourized liquid hydrocarbon fraction, the condensible gaseous hydrocarbon fraction and the water vapour.

The process may then include, in a cooling stage, cooling the treated gas or vapour phase after it has left the distillation zone, thereby to condense at least some of the condensible gaseous hydrocarbon fraction, and returning at least some of this condensed hydrocarbon product to the distillation zone as reflux for the distillation. Thus, the treated gas or vapour phase may typically be cooled to between 30° C. and 50° C., typically to about 40° C., at a pressure as close as practical to the reactor pressure.

By 'non-condensible gaseous hydrocarbon fraction' is meant hydrocarbon product that is in gas or vapour form at the prevailing temperature and pressure conditions in the reactor and which does not condense at the prevailing temperature and pressure conditions in the cooling stage.

On the other hand, by 'condensible gaseous hydrocarbon fraction' is meant hydrocarbon product that is in gaseous or vapour form at the prevailing temperature and pressure conditions in the reactor and which condenses at the prevailing temperature and pressure conditions in the cooling stage, to form the condensed hydrocarbon product of which at least part is returned to the distillation zone as ref lux. By 'vapourized liquid hydrocarbon fraction' is meant hydrocarbon product which is in vapour form at the prevailing temperature and pressure conditions in the reaction zone of the reactor, and which is in liquid form at the prevailing temperature and pressure conditions at the gas phase exit from the distillation zone. The vapourized liquid hydrocarbon fraction is thus heavier, as regards its molecular mass, than the condensible gaseous hydrocarbon fraction. Since the vapourized liquid hydroarbon fraction is in liquid or condensed form at the exit conditions of the distillation zone, it constitutes a portion of the reflux in the distillation zone. The condensed vapourized liquid hydrocarbon fraction which exits the bottom of the distillation zone is also referred to as 'the liquid hydrocarbon fraction'.

By 'liquid hydrocarbon product' is meant product which is in liquid form at the prevailing temperature and pressure conditions in the reactor, and which is in solid or gelled format atmospheric pressure and at a temperature close to ambient temperature. Thus, typically, the liquid hydrocarbon product comprises hydrocarbon molecules containing 20 or more carbon atoms, and thus includes wax.

The distillation may be effected by passing the gas phase upwardly across at least one d installation stage in the distillation zone of the slurry reactor, in countercurrent fashion to the refluxed condensed hydrocarbon product and the liquid hydrocarbon fraction.

The distillation stage may comprise, at least in principle, any suitable gas/liquid contact means used for distillation purposes such as a valve distillation tray, a sieve distillation tray, any other alternative distillation tray, randomly packed distillation media, structurally packed distillation media, or the like; however, a fixed valve distillation tray is preferred.

Preferably, more than one such stage is used, eg at least two vertically spaced stages. However, 3 to 5 such stages, each comprising a distillation tray or layer of media, are preferred.

A collector tray may be located below the lowermost distillation stage, and the liquid collected on the collector tray can thus be routed, eg by means of a conduit, to the slurry bed and/or can be withdrawn from the reactor and/or can be routed to the top of the wash stage for use as washing liquid in the wash stage. This liquid hydrocarbon fraction will mainly consist of liquid formed by condensation of the vapourized liquid hydrocarbon fraction. There is thus no contact of any liquid which is returned to the slurry bed with the gas phase in the freeboard zone, ie there is no washing of entrained catalyst particles or slurry droplets from the gas phase in the freeboard zone. Any liquid which is withdrawn can be mixed with any of the other products withdrawn from the reactor, if desired.

The superficial gas velocity through the fixed valve distillation tray(s) may be in the range 0.2 m/s to 2.0 m/s, preferably about 1 m/s. The superficial gas velocity through the slurry bed is normally lower than the superficial gas velocity through the distillation zone, and hence the effective reactor diameter or cross-sectional dimension will be smaller in the distillation zone than in the reaction zone.

The process may include the washing of the gas phase. The washing of the gas phase may be effected by means of a wash liquid, in a wash zone between the freeboard zone and the distillation zone. The headspace will thus then comprise the freeboard zone, the wash zone, and the distillation zone. Such washing will serve to separate entrained catalyst particles from the gas phase. The washing may be effected by passing the gas phase upwardly across a wash stage in the wash zone in counter-current fashion to the wash liquid.

The wash liquid may be liquid hydrocarbon product. The process may thus include subjecting a portion of the slurry bed to solids separation to remove the majority of the catalyst particles from the liquid hydrocarbon product, thereby producing liquid hydrocarbon product which is then used as the wash liquid.

Since the composition and temperature of the wash liquid is the same as that of the slurry bed suspension liquid, no distillation or fractionation will occur in the wash zone unless liquid from the distillation zone is allowed to enter the wash zone. Thus, in a first embodiment, both the washing of entrained catalyst particles or slurry droplets and distillation may take place in the wash zone, in which case liquid from the distillation zone is allowed to enter the wash zone in addition to wash liquid. However, in a second preferred embodiment, no liquid from the distillation zone enters the wash zone so that only washing of catalyst particles or slurry droplets with the wash liquid takes place in the wash zone. In this embodiment, the liquid from the distillation zone is collected on the distillation zone collector tray as hereinbefore described, and returned to the slurry bed and/or withdrawn from the reactor.

The wash stage may comprise at least one wash tray, and a collector tray below the wash tray, with the wash liquid being introduced into the wash zone or stage above the wash tray, and wash liquid and solids passing from the wash stage to the slurry bed without contact thereof with the gas phase in the freeboard zone, eg by means of a conduit leading from the wash stage collector tray to the slurry bed. Preferably, the wash stage comprises more than one wash tray, eg 2 or 3 wash trays spaced vertically apart. The wash trays may be fixed valve trays.

In the second embodiment, contact between the solid catalyst particles and the reflux liquid, ie refluxed condensed hydrocarbon product and liquid hydrocarbon fraction, is avoided. It has surprisingly been found that contact between the solid catalyst particles and the ref lux liquid in some cases results in break-up and/or loss of catalytic activity of the catalyst particles. In other words, such contact in some cases has a detrimental effect on the desired properties of the catalyst particles. The use of the washing stage overcomes or at least reduces this problem, while retaining the advantages of the distillation zone whose main purpose is then to remove the liquid hydrocarbon product and most of the liquid hydrocarbon fraction from the gas phase before the gases and vapours of the gas. phase leave the distillation zone.

According to a second aspect of the invention, there is provided an installation for producing liquid and, optionally, gaseous products from gaseous reactants, the installation comprising a reactor vessel having a reaction zone which, in use, will contain a slurry bed of solid particles suspended in a suspension liquid, and a distillation zone above the reaction zone;

a gas inlet in the vessel at a low level within the reaction zone, for introducing gaseous reactants into the vessel;

a gas outlet in the vessel in the distillation zone, for withdrawing a gas phase comprising unreacted gaseous reactants and, when present, vapour product from the vessel;

a liquid outlet in the vessel within the reaction zone, for withdrawing liquid product from the vessel;

optionally, a washing stage in a washing zone located below the distillation zone; and a distillation stage in the distillation zone, and in which the gas phase is, in use, subjected to distillation, before exiting the distillation zone through the gas outlet.

The installation may include a cooling stage, operatively connected to the gas outlet of the vessel by means of a first conduit, and a second conduit leading from the cooling stage back to the distillation stage, for returning condensed product from the cooling stage to the distillation stage as reflux.

The distillation stage may be as hereinbefore described. A plurality of distillation stages as also hereinbefore described, may be provided in the distillation zone, which is thus spaced from the reaction zone by a freeboard zone as hereinbefore described, ie containing no gas/liquid contact means such as distillation or washing trays.

The installation may include the washing stage, with the washing stage being located between the freeboard zone and the distillation zone. The washing stage may be as hereinbefore described.

The invention will now be described by way of example, with reference to the accompanying diagrammatic drawings.

BRIEF DESCRIPTION OF THE DRAWINGS

In the drawings

Referring to FIG. 1, reference numeral 10 generally indicates a works pilot plant slurry reactor forming part of an installation according to a first embodiment of the invention, for producing liquid and gaseous or vapour products from gaseous reactants.

Figure 1:
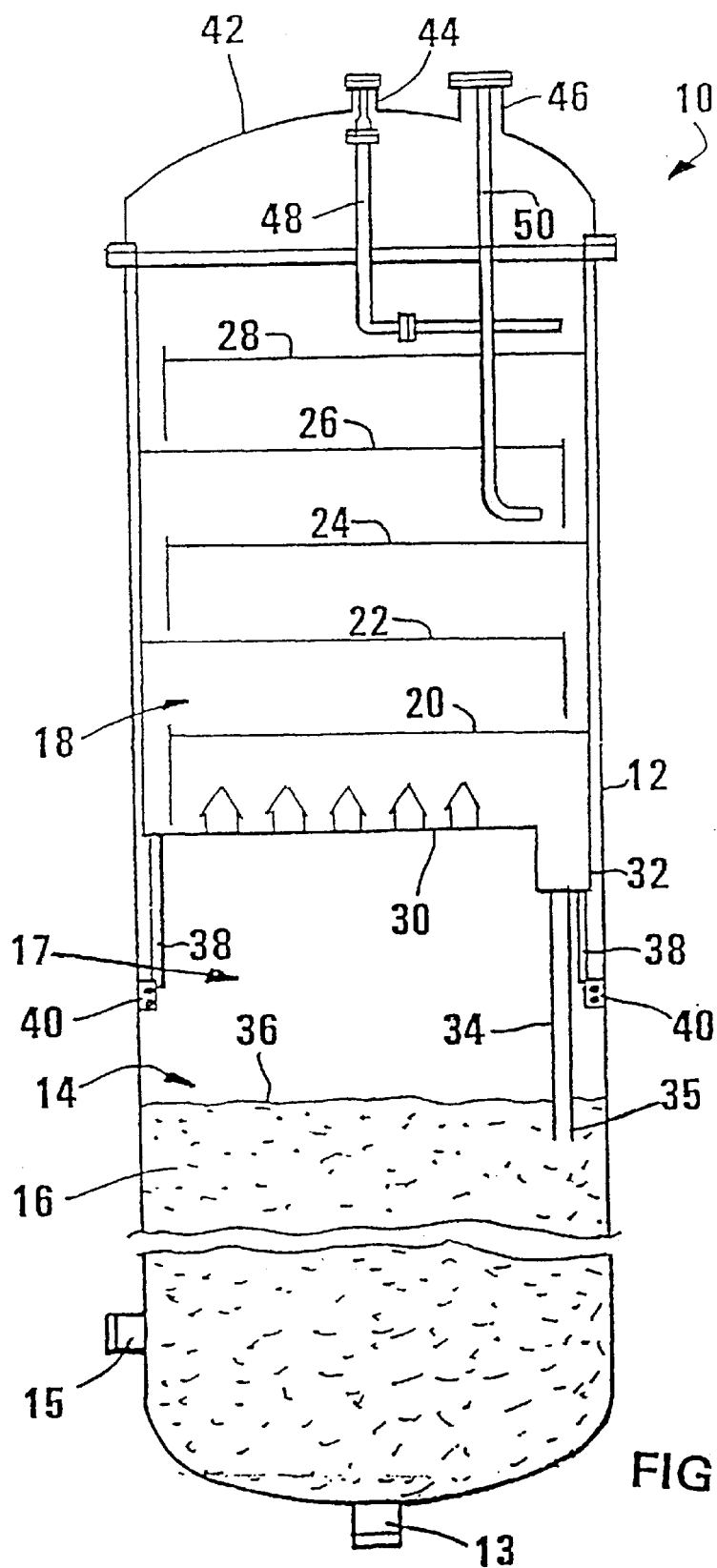
FIG. 1 shows, diagrammatically, a longitudinal sectional view of part of a slurry reactor forming part of a works pilot plant installation according to a first embodiment of the invention, for producing liquid and gaseous products from gaseous reactants.

The reactor 10 includes a cylindrical reactor vessel 12 containing, in a reaction zone 14 thereof, a slurry bed 16 comprising Fischer-Tropsch catalyst particles, typically an iron or cobalt based catalyst, suspended in liquid hydrocarbon product. The vessel 12 is provided with a gas inlet 13 at a low level, ie at the bottom of the slurry bed 16, as well as a slurry outlet 15 for withdrawing slurry from the slurry bed 16.

The vessel 12 also includes a distillation zone, generally indicated by reference numeral 18, in the vessel head space above the slurry bed 16. A freeboard zone 17 is provided between the reaction zone 14 or the slurry bed 16 and the distillation zone 18. The head space thus comprises the freeboard zone 17 and the distillation zone 18. In the distillation zone 18 are mounted five fixed valve distillation trays 20, 22, 24, 26 and 28, with the tray 28 being uppermost. Below the lowermost tray 20 is located a chimney collector tray 30. The tray 30 is provided with a sump or well 32 from which leads a conduit 34. The conduit 34 thus depends downwardly and its lower end 35 is located below the level 36 of the slurry bed 16, eg about 200 mm below the normal slurry bed level. Typically, the maximum slurry bed level is controlled at about 1 m below the lower end of the sump 32. The trays 20 to 30 are supported by support legs 38 mounted to brackets 40 attached to the inside of the vessel 12.

The diameter of the vessel 12, in the distillation zone 18 thereof, is about 870 mm, while the length of the distillation zone 18 is about 8.4 m, with the spacing between adjacent trays being about 460 mm.

The upper end of the vessel 12 is closed off with a domed cap 42 having gas outlet openings 44, 46. Through the gas outlet opening 44 protrudes a reflux conduit 48, with the reflux conduit 48 terminating above the uppermost tray 28. The discharge end of the conduit 48 is provided with a vertical distribution pipe (not shown), having a length of about 450 mm, and along the length of which is located a plurality of vertically spaced outlet openings, each about 8 mm in diameter. Preferably 10 of these openings, more preferably 15 thereof, are provided.

Through the gas outlet 46 protrudes a pumparound conduit 50 terminating above the tray 24. The discharge end of the conduit 50 is similarly provided with an upright distribution pipe along the length of which is located a plurality of evenly vertically spaced 8 mm diameter holes. Preferably 10 of these holes, more preferably 15 thereof, are provided.

During test runs as described hereunder, the reactor 10 was operated to produce gaseous and liquid hydrocarbon products from a synthesis gas fed through the gas inlet 13 into the bottom of the reactor, with the synthesis gas comprising carbon monoxide and hydrogen. The synthesis gas was thus continuously fed into the bottom of the slurry bed 16, while the reactor was operated so as to maintain a constant catalyst slurry bed level. The conditions in the reaction zone 14 were as given in Table 1, with the temperature typically being controlled by means of cooling coils located in or around the slurry bed.

A gas phase comprising non-condensible unreacted gaseous reactants, water vapour, a non-condensible gaseous hydrocarbon fraction, a condensible gaseous hydrocarbon fraction, a vapourized liquid hydrocarbon fraction, liquid hydrocarbon product entrained with the gaseous or vapour components, and solid catalyst particles also entrained with the gaseous or vapour components, passed from the slurry bed, through the freeboard zone 17, and into the distillation zone 18. In the freeboard zone 17, no contact of the gas phase with any liquid occurs, and hence there is no washing of catalyst particles and entrained liquid from the gas phase in the freeboard zone 17. In the distillation zone 18, the gas phase was subjected to distillation by means of the reflux and/or pumparound streams entering along the conduits 48, 50 respectively, at the conditions as specified in Table 1. This distillation served to remove substantially all of the entrained catalyst particles and entrained liquid hydrocarbon product from the gas phase, and also served to distil from the gas phase the liquid hydrocarbon fraction which is at liquid form at the prevailing temperature and pressure conditions at the gas outlets 44, 46.

The treated gas phase exiting through the gas outlets 44, 46 was subjected to single stage cooling/condensation in which the condensible hydrocarbon fraction condenses, and this condensate was returned to the reactor as ref lux along the conduit 48 and/or along the conduit 50 as reflux. In a separate test to demonstrate the effective removal of entrained solids by washing, liquid hydrocarbon product was introduced, along the conduit 50, as washing liquid.

The diameter of the vessel 12 in the distillation zone 18 is such that the superficial gas velocity through the distillation section 18 is usually greater than 0.2 m/sec. The chimney collector tray 30 is of standard design for dirty service, and serves to accumulate liquid product passing downwardly from the trays 20 to 28.

In summary, the pilot plant reactor 10 had the following parameters during test runs conducted on it:

TABLE 1

| Parameter | Value |
| --- | --- |
| Slurry bed 16 height (m) | between 17 and 19 |
| Internal diameter (cm) in the distillation zone 18 | 87 |
| Entrainment separation or distillation zone 18 height (m) | from 20 to 24 |
| Freeboard zone 17 height | 1–2 m |
| Tray (20, 22, 24, 26, 28) type | fixed valve |
| Number of trays | 5 |
| Hydrocarbon condensate feed tray | top (28) or third (24) |
| Top tray temperature (° C.) | ±180 |
| Reaction zone 14 temperature (° C.) | range of between 220 to 250 |
| Reaction zone 14 pressure (bar(g)) | ±20 |

During the pilot plant test runs the hydrocarbon product condensate was fed to the top tray 28 or to the tray 24. When routed to the tray 24, this was equally as effective as when routed to the tray 28. In Examples 1 and 2 hereunder, hydrocarbon product condensate was only fed to the top tray 28. The trays 20 to 28 serve to strip liquid hydrocarbon product and condensed gaseous hydrocarbon product, ie the liquid hydrocarbon fraction, from the refluxed hydrocarbon condensate so that the treated gas phase or fraction withdrawn from the top of the reactor is lighter, and also to prevent carry over of catalyst, entrained liquid hydrocarbon product, and lighter liquid hydrocarbon product, ie the liquid hydrocarbon fraction, with the gas phase from the top of the reactor 10. Hydrocarbon condensate was constantly pumped in at a variable rate at the top of the reactor in order to wash the trays 20 to 28. The temperature of the tray 28 was controlled around a temperature of 180° C. with each successive tray in a downward direction having an increased equilibrium temperature and composition.

The following non-limiting Examples were conducted in test runs using the reactor 10:

EXAMPLE 1

Synthesis gas was fed to the three-phase slurry bed reactor 10 at a flow rate of 6000 $m^3_n$/h. An iron based catalyst, suspended as a slurry in molten wax as slurrying agent, at a concentration of 35 mass %, was used. The gas passed through the reactor, dissolved in the reactor liquid or slurrying agent, and reached the catalyst surface where the Fischer-Tropsch reaction took place. The bed of gas-containing slurry was controlled at a level of 17.4 m from the bottom of the reactor 12, from where droplets of slurry were carried up above this level into the freeboard area or zone 17 of the head space above the slurry bed, and from there into the distillation zone 18. This droplet transport process is termed 'entrainment'. In the distillation zone 18, five trays were used to separate the droplets from the gas phase and to minimize the catalyst loss through the top of the reactor. For this particular example the catalyst entrainment in the tail gas exiting the reactor was measured at 2.15 mg solids/$m^3_n$/h, whereas it is normally about 10.4 mg/$m^3_n$/h when no entrainment separation is practised in the reactor 10.

EXAMPLE 2

Synthesis gas was fed to the three-phase slurry bed reactor 10 at a flow rate of 8800 $m^3_n$/h. A cobalt based catalyst, suspended as a slurry in molten wax as slurrying agent, at a concentration of 30 mass %, was used. The process reaction conditions were further identical al to those described in Example 1. For this particular example the catalyst entrainment in the tail gas was measured at 0.015 mg/$m^3_n$/h, whereas it is normally about 0,074 mg/$m^3_n$/h when no entrainment separation is practised in the reactor 10.

Figure 2:
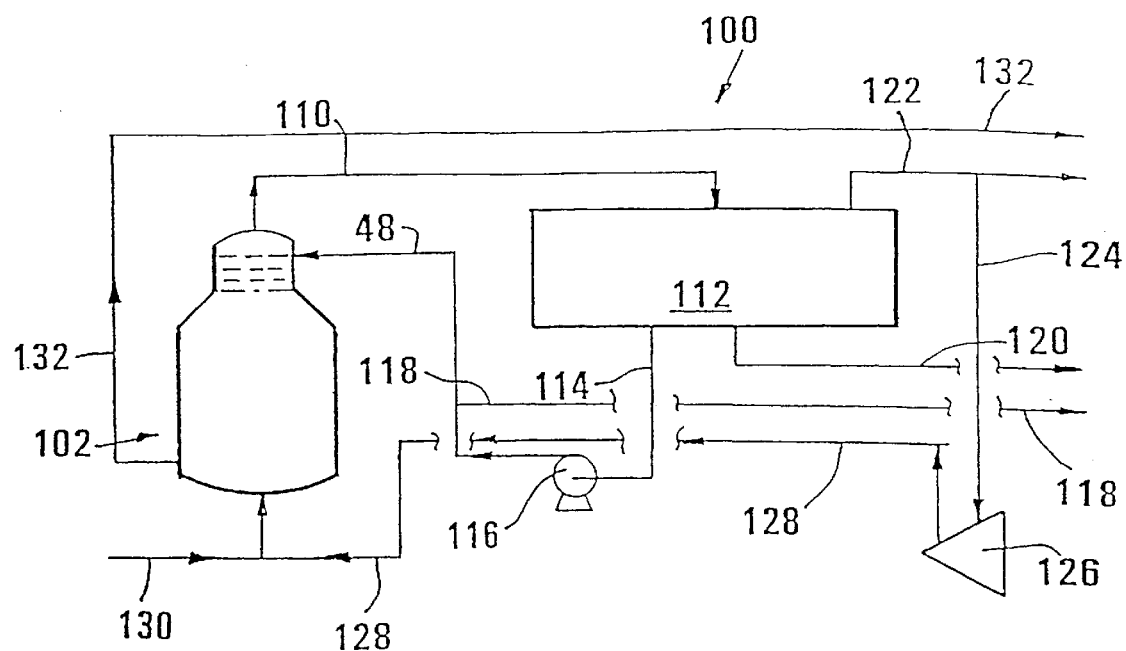
FIG. 2 shows a flow diagram of an installation according to a second embodiment of the invention, for producing liquid and gaseous or vapour products from gaseous reactants.
Figure 3:
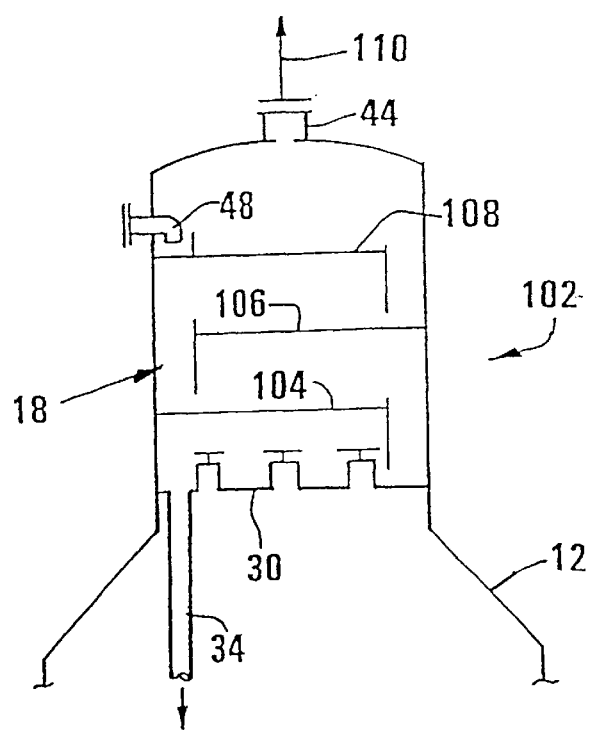
FIG. 3 shows, diagrammatically, a longitudinal sectional view of part of the slurry reactor shown in FIG. 2.

Referring to FIGS. 2 and 3, reference numeral 100 generally indicates an installation according to another embodiment of the invention, for producing liquid and gaseous products from gaseous reactants.

The installation 100 includes a reactor 102 which is similar to the reactor 10 hereinbefore described with reference to FIG. 1. Parts of the reactor 102 which are the same or similar to those of the reactor 10, are indicated with the same reference numerals.

However, the reactor 102 only contains, in its distillation zone 16, three fixed valve distillation trays 104, 106, 108, with the tray 108 being uppermost and the ref lux conduit 48 terminating above the plate 108. The reactor 102 also includes a chimney collector tray 30 below the lowermost distillation tray 104 with the conduit 34 leading directly from the collector tray 30.

The installation 100 includes a gas withdrawal conduit 110 leading from the gas outlet 44 to a single stage cooling and condensing stage 112. A condensed hydrocarbon fraction or product withdrawal line 114 leads from the stage 112 to a pump 116. The reflux conduit 48 leads from the pump 116; however, a condensed hydrocarbon fraction or product withdrawal line 118 also leads from the reflux line 48 for withdrawing condensed product as desired. A water withdrawal conduit 120 also leads from the stage 112.

Similarly, a tail gas conduit 122, for withdrawing unreacted synthesis gas as well as a non-condensible hydrocarbon fraction or product gas, leads from the stage 112. A recycle gas conduit 124 leads from the conduit 122 to a compressor 126, with a recycle conduit 128 leading from the compressor 126 to the gas inlet 13 at the bottom of the reactor 102. The conduit 128 is joined by a fresh synthesis gas feed conduit 130.

A slurry withdrawal conduit 132 leads from the slurry outlet 15 of the reactor.

The reactor 102 functions in substantially identical fashion to the reactor 10, with condensed hydrocarbon fraction being refluxed to the top of the tray 108 along the conduits 114, 48. Tail gas is withdrawn from the installation along the line 122 or is recycled back to the reactor along the lines 124, 128, 130.

The maximum level of the slurry bed is typically controlled at between 1 m and 2 m below the level at which the swaged or outwardly flaring portion of the vessel 12 is joined to its cylindrical wall portion.

Figure 4:
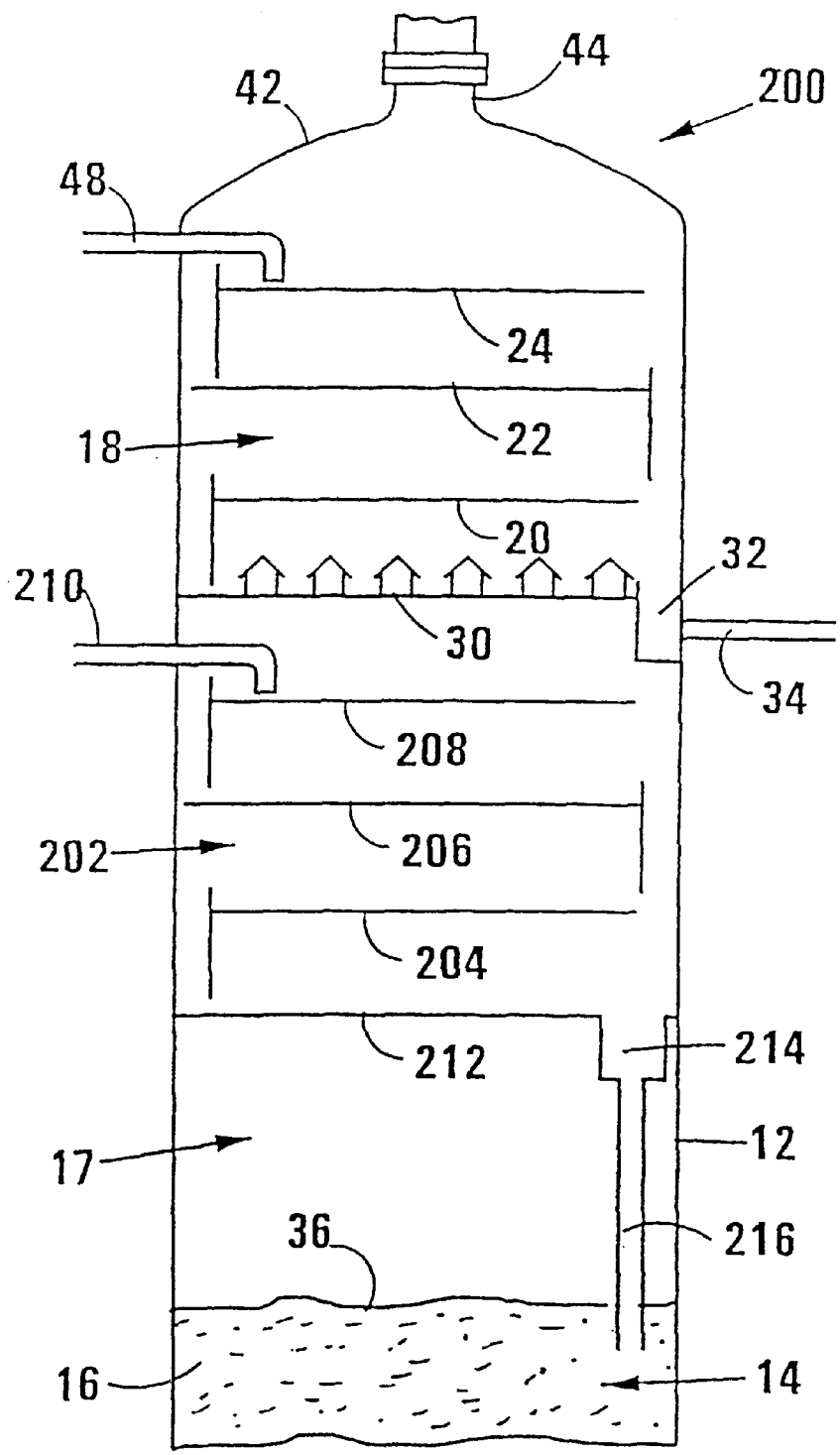
FIG. 4 shows, diagrammatically, a longitudinal sectional view of part of a slurry reactor forming part of an installation according to a third embodiment of the invention.

Referring to FIG. 4, reference numeral 200 generally indicates slurry reactor forming part of an installation according to a third embodiment of the invention, for producing liquid and gaseous or vapour products from gaseous reactants.

Parts of the reactor 200 which are the same of similar to those of the reactor 10 are indicated with the same reference numerals.

The head space of the reactor 200 comprises, in addition to the freeboard zone 17 and distillation zone 18, a wash zone 202. The wash zone 202 is located between the freeboard zone 17 and distillation zone 18.

The distillation zone 18 of the reactor 200 only contains 3 fixed valve distillation trays 20, 22 and 24, with the reflux conduit 48 discharging condensed hydrocarbon product reflux onto the uppermost tray 24. Further, the conduit 34 which leads from the collector tray sump 30, is arranged to withdraw liquid hydrocarbon fraction from the reactor, rather than returning it to the slurry bed 16.

The wash zone 202 contains a wash stage comprising three vertically staggered fixed valve wash trays 204, 206 and 208, with the tray 208 being uppermost. A wash liquid conduit 210 is arranged to discharge liquid hydrocarbon product as wash liquid onto the uppermost wash tray 208. The liquid hydrocarbon product used as wash liquid is obtained by subjecting a portion of the slurry bed to solids separation to remove the majority of the catalyst particles therefrom. A collector tray 212 is located below the lowermost wash tray 204 and is provided with a sump or well 214. A wash liquid return conduit 216, for returning used wash liquid containing catalyst particles washed from the gas phase in the wash zone 202 to the slurry bed 16, leads from the sump 214 into the slurry bed.

Slurry reactors, such as the reactors 10, 102, are well known three phase reactors comprising a liquid phase in which solid catalyst particles are dispersed or held in suspension by a gas phase bubbling through the liquid phase. The liquid and suspended solid phase constitute the slurry. Catalyst dispersion may also be enhanced by creating an upward velocity of the liquid phase.

As the gas bubbles reach the upper surface of the slurry bed, they break through the upper surface with sufficient energy to entrain some of the slurry. Due to the drag force of the upward flowing gas and the downward pull of gravity larger droplets return to the top of the slurry bed but lighter droplets are carried upward. Slurry entrainment flux increases with increasing gas velocity and gas viscosity. The solids content of the entrained slurry increases with increasing bulk slurry solids concentration and, especially, with increases in the concentration of solids having a size of less than 10 microns.

The slurry losses from the reactor will increase with higher entrainment rates of slurry so that the reactor diameter in known reactors not having a distillation zone 16, is large in the freeboard region above the slurry surface to avoid high velocities in this region.

To reduce catalyst losses in such known reactors, entrainment separation is normally accomplished with internal separators. There are a number of known separator designs, which rely on a change in direction of the gaseous vapour flow while the gas or vapour travels at a high velocity. These designs make use of entrainment separation techniques which cause the entrained slurry droplets to coalesce and fall back into the slurry bed. Such units also allow for free draining to prevent accumulation of catalyst particles and possible pluggage. A typical example of such a unit is a vane type entrainment separator. These separators cause the slurry droplets to impact on a metal surface by rapidly changing the direction of the gas flow. However, the known entrainment separation devices are not 100% efficient in removing the entrained slurry. Moreover, at the operating conditions of the slurry reactors used for the Fischer-Tropsch processes, some of the reactor liquid components are in the vapour phase, as hereinbefore described, and cannot be separated by these known devices.

The basic Fischer Tropsch reaction is:

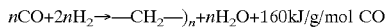

$$nCO+2nH_2 \rightarrow -CH_2-)_n + nH_2O + 160 kJ/g/mol\ CO$$

In this exothermic reaction, the heat of reaction is typically removed by pumping boiler feed water through coils submerged in the slurry bed. In normal slurry bed reactor operations for the Fischer Tropsch synthesis process it was found that about 50% by weight of the hydrocarbons synthesised were too heavy to escape the reactor with the unreacted gas, and comprise most of the reactor liquid phase. It is possible to separate most of the remaining products from the unreacted gas by multi-stage condensation to form some reactor liquid components, light hydrocarbon products and reaction water.

The Applicant has surprisingly found that by using fixed valve distillation trays commonly used in distillation column designs for liquid separations, substantially more effective separation of both reactor liquid and catalyst from the gas phase can be achieved.

More particularly, the Applicant has surprisingly found that with the application of distillation trays in accordance with the invention, effective separation could be achieved with only three fixed valve distillation trays. The present invention has further surprising advantages, viz the complete removal of the entrained reactor liquid and catalyst from the gas phase; all the reactor liquid fractions that are present in the vapour phase are condensed and retained in the Fischer-Tropsch reactor; and it permits the reactor diameter to be reduced in the freeboard region above the slurry interface in the Fischer-Tropsch reactor since the separation efficiency is not determined by the slurry entrainment rate.

The retention of all the reactor liquid within the Fischer-Tropsch reactor makes it possible to separate the lighter hydrocarbon products from the reactor product gases and vapours in a single condensation step rather than the minimum of two condensation steps required for the prior art. Known reactors require two steps to avoid the blockage of heat exchange surfaces with solid wax at the temperatures required to condense all the desired liquid products.

We claim:

1. A process for producing liquid and gaseous products from gaseous reactants, which process comprises feeding, at a low level, a synthesis gas stream comprising mainly carbon monoxide and hydrogen, as gaseous reactants, into a slurry bed of solid Fischer-Tropsch catalyst particles suspended in a suspension liquid, with the slurry bed being provided in a reaction zone;

allowing the gaseous reactants to react, by means of Fischer-Tropsch synthesis, as they pass upwardly through the slurry bed, thereby to form liquid and gaseous products, with the gaseous reactants and the gaseous product assisting in maintaining the solid catalyst particles in suspension in the suspension liquid, and with the liquid product forming, together with the suspension liquid, a liquid phase of the slurry bed;

withdrawing liquid phase from the slurry bed, to maintain the slurry bed at a desired level;

allowing gaseous products and unreacted gaseous reactants to disengage from the slurry bed and to pass upwardly, together with entrained solid catalyst particles and liquid phase, as a gas phase into a freeboard zone of a head space above the slurry bed, with the freeboard zone being located immediately above the reaction zone;

treating the gas phase by subjecting it to distillation and, optionally, washing in the head space, with the distillation being effected in a distillation zone of the head space, and the washing, when present, being effected in a wash zone of the head space, and with the distillation zone and the wash zone, when present, being spaced from the reaction zone by the freeboard zone, thereby to separate entrained solid catalyst particles and liquid phase from the gas phase;

returning the separated entrained solid catalyst particles and liquid phase from the distillation zone, or, when present, from the wash zone, to the slurry bed through a conduit so that there is no contact thereof with the gas phase in the freeboard zone; and withdrawing the treated gas phase from the head space.

2. A process according to claim 1, wherein the suspension liquid is the liquid product; and wherein the slurry bed and the head space are provided in a slurry reactor.

3. A process according to claim 2, wherein the gas phase entering the head space comprises non-condensible unreacted gaseous reactants, a non-condensible gaseous hydrocarbon fraction, entrained solid catalyst particles, entrained liquid hydrocarbon product, a vapourized liquid hydrocarbon fraction, a condensible gaseous hydrocarbon fraction, and water vapour, while the treated gas phase which is withdrawn from the distillation zone comprises the non-condensible unreacted gaseous reactants, the non-condensible gaseous hydrocarbon fraction, the condensible gaseous hydrocarbon fraction, and the water vapour, and the gaseous hydrocarbon products comprise the non-condensible gaseous hydrocarbon fraction, the vapourized liquid hydrocarbon fraction, the condensible gaseous hydrocarbon fraction and the water vapour.

4. A process according to claim 3, which includes, in a cooling stage, cooling the treated gas or vapour phase after it has left the distillation zone, thereby to condense at least some of the condensible gaseous hydrocarbon fraction, and returning at least some of this condensed hydrocarbon product to the distillation zone as reflux for the distillation.

5. A process according to claim 4, wherein the treated gas or vapour phase is cooled to between 30° C. and 50° C.

6. A process according to claim 4, wherein the distillation is effected by passing the gas phase upwardly across at least one distillation stage in the distillation zone of the slurry reactor, in countercurrent fashion to the refluxed condensed hydrocarbon product and the liquid hydrocarbon fraction.

7. A process according to claim 6, wherein a plurality of vertically spaced distillation stages are used, with each stage comprising a fixed valve distillation tray.

8. A process according to claim 7, wherein the superficial gas velocity through the fixed valve distillation trays is in the range 0.2 m/s to 2.0 m/s, with the superficial gas velocity through the slurry bed normally being lower than the superficial gas velocity through the distillation zone so that the effective reactor diameter or cross-sectional dimension is smaller in the distillation zone than in the reaction zone.

9. A process according to claim 7, wherein a collector tray is located below the lowermost distillation stage, with the liquid which collects on the collector tray being returned to the slurry bed by means of the conduit, so that there is thus no contact of the liquid which is returned to the slurry bed with the gas phase in the freeboard zone.

10. A process according to claim 4, which includes the washing of the gas phase in the wash zone, with the washing thereof being effected by means of a wash liquid, and with the washing thus serving to separate entrained catalyst particles from the gas phase.

11. A process according to claim 10, wherein the washing is effected by passing the gas phase upwardly across a wash stage in the wash zone in counter-current fashion to the wash liquid, with the wash liquid being liquid hydrocarbon product.

12. A process according to claim 11, which includes subjecting a portion of the slurry bed to solids separation to remove the majority of the catalyst particles from the liquid hydrocarbon product, thereby producing liquid hydrocarbon product which is then used as the wash liquid.

13. A process according to claim 12, wherein both the washing of entrained catalyst particles or slurry droplets and distillation takes place in the wash zone, with liquid from the distillation zone being allowed to enter the wash zone in addition to the wash liquid.

14. A process according to claim 12, wherein no liquid from the distillation zone enters the wash zone so that only washing of catalyst particles or slurry droplets with the wash liquid takes place in the wash zone.

15. A process according to claim 11, wherein the wash stage comprises at least one wash tray, and a collector tray below the wash tray, with the wash liquid being introduced into the wash zone or stage above the wash tray, and the wash liquid passing, together with the solid catalistic particles, from the wash stage to the slurry bed by means of the conduit, which thus leads from the wash stage collector tray to the slurry bed.

16. A process according to claim 15, wherein the wash stage comprises a plurality of wash trays spaced vertically apart, with the wash trays being fixed valve trays.

* * * * *